(12) United States Patent
Tada (10) Patent No.: US 10,996,349 B2
(45) Date of Patent: May 4, 2021

(54) X-RAY SIGNAL PROCESSOR AND X-RAY SPECTROMETER

(71) Applicant: Rigaku Corporation, Akishima (JP)

(72) Inventor: Tsutomu Tada, Ibaraki (JP)

(73) Assignee: RIGAKU CORPORATION, Tokyo (JP)

( * ) Notice: Subject to any disclaimer, the term of this patent is extended or adjusted under 35 U.S.C. 154(b) by 55 days.

(21) Appl. No.: 16/697,200

(22) Filed: Nov. 27, 2019

(65) Prior Publication Data

US 2020/0166657 A1 May 28, 2020

(30) Foreign Application Priority Data

Nov. 27, 2018 (JP) .............................. JP2018-221141

(51) Int. Cl.
*G01T 1/24* (2006.01)
*A61B 6/00* (2006.01)

(52) U.S. Cl.
CPC .............. *G01T 1/244* (2013.01); *A61B 6/585* (2013.01); *G01T 1/247* (2013.01); *A61B 6/4208* (2013.01)

(58) Field of Classification Search
CPC .......... G01T 1/244; G01T 1/247; A61B 6/585; A61B 6/4208
See application file for complete search history.

(56) References Cited

FOREIGN PATENT DOCUMENTS

| JP | H06-123778 A | 5/1994 |
|---|---|---|
| JP | H10-318946 A | 12/1998 |
| JP | 2010-008176 A | 1/2010 |
| JP | 2016-125922 A | 7/2016 |

OTHER PUBLICATIONS

Glenn F. Knoll, "Radiation Detection and Measurement (3rd Edition)", Nikkan Kogyo Shimbun, Mar. 27, 2001, p. 435-436 (11.5.1 Leakage Current), p. 691-701 (17.5.1 Preamplifier), (cited in "Description of the Related Art", on p. 2, line 17 to 26 of the specification.).

*Primary Examiner* — Edwin C Gunberg
(74) *Attorney, Agent, or Firm* — HEA Law PLLC (57) ABSTRACT

Provided is an X-ray signal processor and an X-ray spectrometer that are configured to measure X-rays and, at the same time, accurately detect, with a simple method, the degree of performance degradation of a semiconductor detector. The X-ray signal processor includes: a semiconductor detector configured to generate a charge corresponding to energy of detected X-rays; a preamplifier configured to output a ramp voltage signal corresponding to the generated charge; a counter configured to count the X-rays for each voltage change amount due to the charge based on the ramp voltage signal; and a judgment part configured to determine whether the semiconductor detector has been degraded based on a first voltage change evaluation value corresponding to a total sum of products of the voltage change amount and an occurrence frequency thereof, and a second voltage change evaluation value corresponding to an increase amount of the ramp voltage signal.

8 Claims, 7 Drawing Sheets

X-RAY SIGNAL PROCESSOR AND X-RAY SPECTROMETER

CROSS-REFERENCE TO RELATED APPLICATION

The present discloser relates to the subject matter contained in the Japanese Patent Application No. JP2018-221141 filed on Nov. 27, 2018, which is expressly incorporated herein by reference in its entirety.

BACKGROUND OF THE INVENTION

1. Field of the Invention

The present invention relates to an X-ray signal processor and an X-ray spectrometer each using a semiconductor detector.

2. Description of the Related Art

An X-ray spectrometer is known as an apparatus configured to analyze elements contained in a sample and measure the concentrations of the elements and is configured to detect secondary X-rays emitted when the sample is irradiated with, for example, primary X-rays or electron beams, to thereby analyze constituent elements from the energy and intensity of the secondary X-rays.

There are two types of the X-ray spectrometers which are a wavelength-dispersive X-ray spectrometer and an energy-dispersive X-ray spectrometer. The wavelength-dispersive X-ray spectrometer uses a spectroscopic device to spectrally disperse secondary X-rays emitted from a sample for each wavelength, and discriminately detects secondary X-rays having a specific wavelength. The energy-dispersive X-ray spectrometer uses a semiconductor detector or other such detector having a high energy resolution to detect secondary X-rays emitted from a sample.

The energy-dispersive X-ray spectrometer uses the detector to directly detect secondary X-rays emitted from a sample. It is thus possible to simultaneously obtain information on a plurality of wavelengths without scanning the spectroscopic device and the detector, unlike in the case of the wavelength-dispersive X-ray spectrometer. Therefore, the energy-dispersive X-ray spectrometer has a feature that more elements can be analyzed in a shorter time with a simpler apparatus configuration than in the case of the wavelength-dispersive apparatus (see Japanese Patent Application Laid-open No. Hei 10-318946).

The detector to be used for the energy-dispersive X-ray spectrometer is required to have a high energy resolution. Therefore, the detector to be used for the energy-dispersive X-ray spectrometer is a Si (Li) detector, a silicon drift detector (SDD detector), or other such semiconductor detector, and is used together with an active reset preamplifier having a low noise level (see Glenn F. Knoll, "Radiation Detection and Measurement (3rd Edition)", Nikkan Kogyo Shimbun, Mar. 27, 2001, p. 435-436 (11.5.1 Leakage Current), p. 691-701 (17.5.1 Preamplifier)).

However, the above-mentioned semiconductor detector is damaged by long-term X-ray irradiation, which degrades its performance. The energy-dispersive X-ray spectrometer cannot perform accurate measurement when the performance of the semiconductor detector is degraded and the energy resolution deteriorates.

Therefore, it is desirable to replace the semiconductor detector before the performance starts to be degraded beyond a predetermined criterion defined in advance. Further, the performance of the semiconductor detector is degraded due to not only damage caused by X-ray irradiation but also a failure of an electrical circuit, insufficient cooling of the semiconductor detector, and other such causes.

In view of the foregoing, there have been related arts involving measuring and evaluating a leakage current flowing through the semiconductor detector. When the semiconductor detector is operated in a steady state, the leakage current normally has a constant steady value. That is, a sudden change or increase in leakage current indicates that the performance of the semiconductor detector has changed.

In "Radiation Detection and Measurement (3rd Edition)", it is disclosed that, in order to detect a leakage current, an ammeter, a current setting apparatus, a current comparator, or other such apparatus is connected to the semiconductor detector, to thereby monitor the leakage current.

In Japanese Patent Application Laid-open No. 2010-8176, it is disclosed that a time interval (ramp period) of an occurrence of a reset in a reset circuit of the semiconductor detector is detected instead of the leakage current when the X-ray spectrometer is turned on. Specifically, in the semiconductor detector, as the value of the current flowing through the semiconductor detector increases, the time interval of the occurrence of a reset becomes shorter. In contrast, as the current decreases, the time interval becomes longer. Hence, it is determined whether or not the time interval is equal to or longer than a predetermined time period, to thereby determine whether or not the spectrometer is ready for analysis.

In Japanese Patent Application Laid-open No. Hei 06-123778, it is disclosed how to prevent a failure of a semiconductor detection device. Specifically, the number of pulses in inhibit signals for resetting is counted. When the count value becomes larger than the set value, it is determined that a severe state where an excessive amount of X-ray energy enters the semiconductor detection device has occurred. When it is determined that the severe state has occurred, a failure of the semiconductor detection device can be prevented by turning off a high voltage generation circuit configured to supply a high voltage to the radiation source.

In Japanese Patent Application Laid-open No. 2016-125922, it is disclosed that X-rays for each pulse height detected by the semiconductor detector are counted and accumulated, and when the counting result reaches a criterion set in advance, it is notified by notification means that a time to replace the semiconductor detector has come.

SUMMARY OF THE INVENTION

In "Radiation Detection and Measurement (3rd Edition)" described above, a dedicated measurement circuit including an ammeter monitors a current flowing through a semiconductor detector to determine whether or not the semiconductor detector is satisfactory. However, the magnitude of the monitored current changes depending not only on the performance degradation of the semiconductor detector but also on a signal current generated when, for example, X-rays are detected. The magnitude of the current also varies depending on the energy and intensity of the detected X-rays.

For that reason, when the current flowing through the semiconductor detector changes, it is impossible to distinguish whether the change has been caused by an abnormality of the semiconductor detector or by variations in intensity and energy of X-rays ascribable to an apparatus (including an X-ray tube and a measured sample) other than the semiconductor detector. Therefore, it is impossible to correctly grasp the state of the semiconductor detector based only on the value of the current flowing through the semiconductor detector.

In Japanese Patent Application Laid-open No. 2010-8176 described above, the time interval of the occurrence of a reset signal in the reset circuit of the semiconductor detector is detected when the apparatus starts up. Immediately after activating the apparatus, the semiconductor detector does not detect florescent X-rays. This method is a method of evaluating the performance of the semiconductor detector by detecting the time interval of the occurrence of a reset while the apparatus is being turned on, that is, during a period during which the semiconductor detector does not detect florescent X-rays.

Therefore, it is impossible with the above-mentioned method to detect the performance degradation of the semiconductor detector after the apparatus is turned on. In addition, it is a precondition that the semiconductor detector does not detect florescent X-rays, and hence the performance of the semiconductor detector cannot be evaluated during the measurement.

Meanwhile, an X-ray spectrometer is generally used continuously as long as there is no failure or other such trouble after turning on. For that reason, it is impossible with the above-mentioned method to detect and notify the performance degradation of the semiconductor detector in a general way of using the X-ray spectrometer.

In Japanese Patent Application Laid-open No. Hei 06-123778 described above, the number of pulses in inhibit signals for resetting is counted, and the total sum of energy of X-rays that have entered the semiconductor detector is obtained from the number of pulses in inhibit signals. This method involves estimating damage caused to the semiconductor detector from the total sum of energy of X-rays that have entered the semiconductor detector, and therefore presupposes that there is a certain correlation between the total sum of energy of X-rays and the performance degradation of the semiconductor detector.

Therefore, it is required to confirm and verify in advance what kind of correlation there is. In addition, actual semiconductor detectors exhibit individual differences in performance, and hence the degree of performance degradation differs for each individual semiconductor detector. However, in the above-mentioned method, the individual differences in performance cannot be taken into consideration.

In Japanese Patent Application Laid-open No. 2016-125922 described above, the X-ray intensity for each kind of energy is used as a parameter to estimate damage caused to the semiconductor detector. This method presupposes that there is a certain correlation between the X-ray intensity and the performance degradation of the semiconductor detector.

Therefore, in the same manner as in Japanese Patent Application Laid-open No. Hei 06-123778 described above, it is required to confirm and verify in advance what kind of correlation there is, and hence individual differences in performance cannot be taken into consideration. In addition, performance degradation cannot be detected by the above-mentioned method when the performance degradation has occurred due to a failure of the electrical circuit, insufficient cooling of the semiconductor detector, or other such causes other than irradiation damage.

The present invention has been made in view of the above-mentioned problems, and has an object to provide an X-ray signal processor and an X-ray spectrometer that are configured to measure X-rays and, at the same time, accurately detect, by a simple method, the degree of performance degradation of a semiconductor detector caused by damage due to X-ray irradiation, a failure of an electrical circuit, insufficient cooling of the semiconductor detector, and other various causes.

According to one aspect of the present invention, there is provided an X-ray signal processor including: a semiconductor detector configured to generate a charge corresponding to energy of detected X-rays; a preamplifier configured to output a ramp voltage signal corresponding to the generated charge; a counter configured to count the X-rays for each voltage change amount due to the charge based on the ramp voltage signal; and a judgment part configured to determine whether the semiconductor detector has been degraded based on a first voltage change evaluation value corresponding to a total sum of products of the voltage change amount and an occurrence frequency thereof, and a second voltage change evaluation value corresponding to an increase amount of the ramp voltage signal.

In the above-mentioned aspects of the invention, the first voltage change evaluation value includes a value obtained by dividing an amplitude of the ramp voltage signal by a sum of the total sum and a value of a leakage current flowing through the semiconductor detector in a normal state.

In the above-mentioned aspects of the invention, each cycle of the ramp voltage signal includes: a reset period that is active from when the ramp voltage signal reaches an upper limit value until the ramp voltage signal is reduced to a lower limit value; and a detection period other than the reset period, and the second voltage change evaluation value includes a value corresponding to one of a slope and the increase amount of the ramp voltage signal in the detection period.

In the above-mentioned aspects of the invention, the X-ray signal processor further includes a cycle measuring part configured to measure a cycle of the ramp voltage signal, wherein the second voltage change evaluation value includes the cycle of the ramp voltage signal measured by the cycle measuring part, and wherein the judgment part is configured to determine whether the semiconductor detector has been degraded based on a first threshold value set in advance and one of a difference and a ratio between the first voltage change evaluation value and the second voltage change evaluation value.

In the above-mentioned aspects of the invention, the judgment part is configured to determine whether to perform the determination based on the total sum and a second threshold value set in advance.

In the above-mentioned aspects of the invention, the X-ray signal processor further includes: a storage part configured to continuously store one of the difference or the ratio between the first voltage change evaluation value and the second voltage change evaluation value; and a prediction part configured to predict a time at which the semiconductor detector will be degraded, from a transition of the stored one of the difference or the ratio.

In the above-mentioned aspects of the invention, the X-ray signal processor further includes a cycle measuring part configured to measure a cycle of the ramp voltage signal, wherein the first voltage change evaluation value includes the total sum, wherein the second voltage change evaluation value includes the cycle of the ramp voltage signal measured by the cycle measuring part, and wherein the judgment part is configured to determine whether the semiconductor detector has been degraded based on a value obtained by subtracting the first voltage change evaluation value from a value obtained by dividing an amplitude of the ramp voltage signal by the second voltage change evaluation value.

In the above-mentioned aspects of the invention, there is provided an X-ray spectrometer including: a semiconductor detector configured to detect X-rays emitted by irradiating a sample with exciting lines, to thereby generate a charge corresponding to energy of the X-rays; a preamplifier configured to output a ramp voltage signal corresponding to the generated charge; a counter configured to count the X-rays for each voltage change amount due to the charge based on the ramp voltage signal; a judgment part configured to determine whether the semiconductor detector has been degraded based on a first voltage change evaluation value corresponding to a total sum of products of the voltage change amount and an occurrence frequency thereof and a second voltage change evaluation value corresponding to an increase amount of the ramp voltage signal; and an analyzer configured to analyze elements in the sample based on the counted X-rays.

According to the present invention, it is possible to produce an X-ray signal processor and an X-ray spectrometer, which are capable of determining whether or not a semiconductor detector has been degraded and of accurately evaluating the degree of performance degradation while measuring X-rays. Since it is possible to determine whether or not the semiconductor detector has been degraded during the measurement, it is not necessary to, for example, stop the measurement and turn on or turn off the spectrometer. Even when there are variations among individual semiconductor detectors, it is possible to accurately grasp the degree of performance degradation for each individual detector. In addition, even when a failure occurs in the X-ray spectrometer and the X-ray signal processor, it is possible to identify the location of the failure by discriminating whether the failure has been caused by the semiconductor detector or by a problem in a circuit in a subsequent stage.

DETAILED DESCRIPTION OF THE INVENTION

Figure 1:
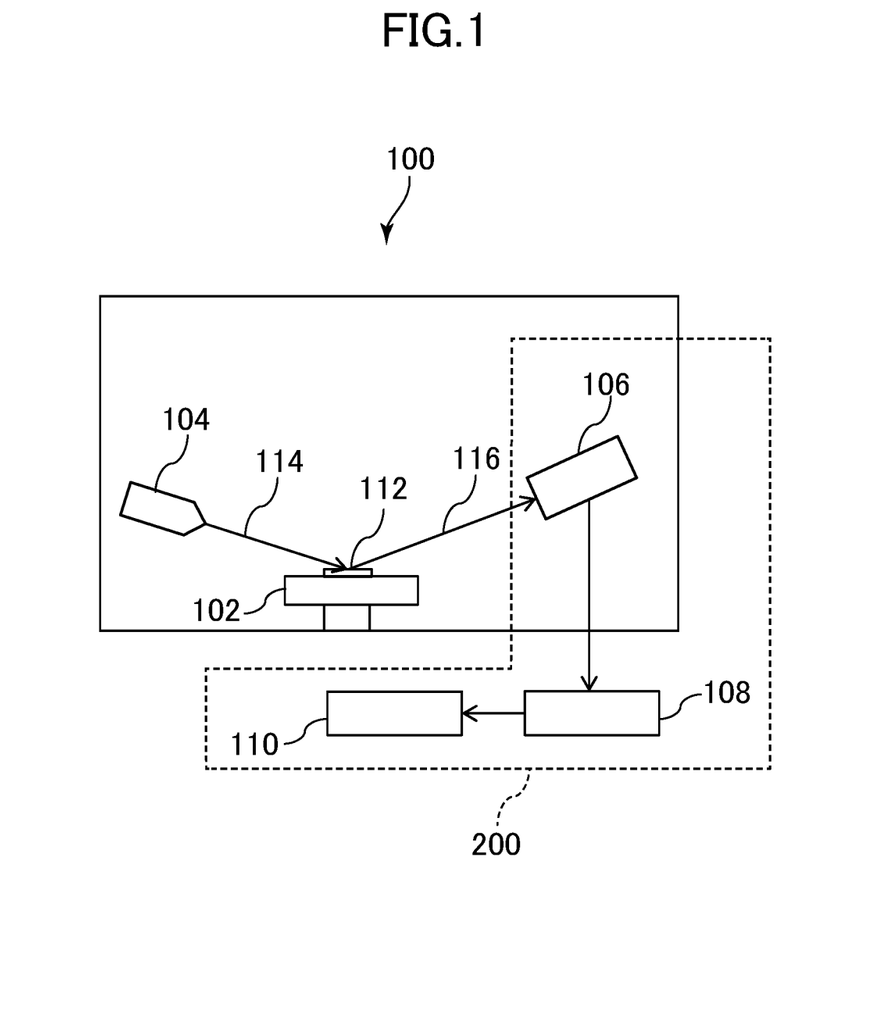
FIG. 1 is a diagram for schematically illustrating an X-ray spectrometer according to at least one embodiment of the present invention.
Figure 2:
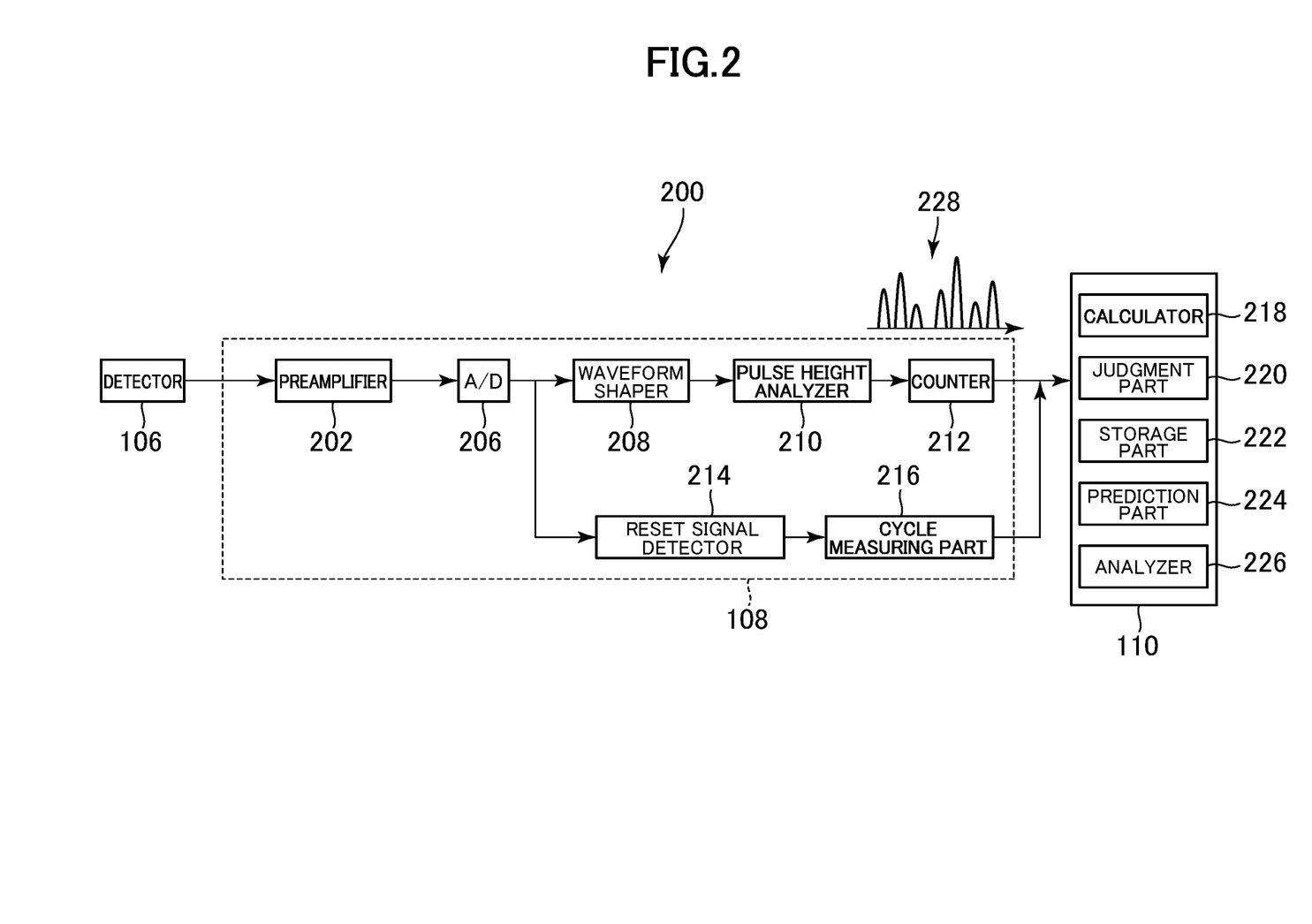
FIG. 2 is a diagram for schematically illustrating an X-ray signal processor according to at least one embodiment of the present invention.

Now, at least one preferred embodiment for carrying out the present invention (hereinafter referred to simply as embodiment) will be described. FIG. 1 is a diagram for schematically illustrating an X-ray spectrometer 100 according to at least one embodiment of the present invention. FIG. 2 is a diagram for schematically illustrating an X-ray signal processor 200 according to at least one embodiment of the present invention.

The X-ray spectrometer 100 includes a sample stage 102, an X-ray source 104, and an X-ray signal processor 200. The X-ray signal processor 200 includes a semiconductor detector 106, a processing unit 108, and an arithmetic operation unit 110. The processing unit 108 includes a preamplifier 202, an A/D converter 206, a waveform shaper 208, a pulse height analyzer 210, a counter 212, a reset signal detector 214, and a cycle measuring part 216.

A sample 112 is placed on the sample stage 102. The sample 112 is a target for elemental analysis.

The X-ray source 104 generates primary X-rays 114, and irradiates the surface of the sample 112 with the primary X-rays 114. Specifically, for example, the X-ray source 104 narrows X-rays emitted from an X-ray tube (not shown) using a collimator (not shown), removes continuous X-ray components using a filter (not shown), and irradiates the surface of the sample 112 with the primary X-rays 114 converted into quasi-monochromatic rays. Secondary X-rays 116 are emitted from the sample 112 irradiated with the primary X-rays 114.

The semiconductor detector 106 generates a charge corresponding to the energy of the detected X-ray. Specifically, for example, the semiconductor detector 106 detects X-rays (secondary X-rays 116) emitted by irradiating the sample 112 with exciting lines (primary X-rays 114), to thereby generate a charge corresponding to the energy of the X-rays (secondary X-rays 116). The semiconductor detector 106 is, for example, a Si (Li) detector, an SDD detector, or other such semiconductor detector.

The preamplifier 202 outputs a ramp voltage signal corresponding to the generated charge. Specific examples of the semiconductor detector 106 and the preamplifier 202 will be described with reference to FIG. 3.

Figure 3:
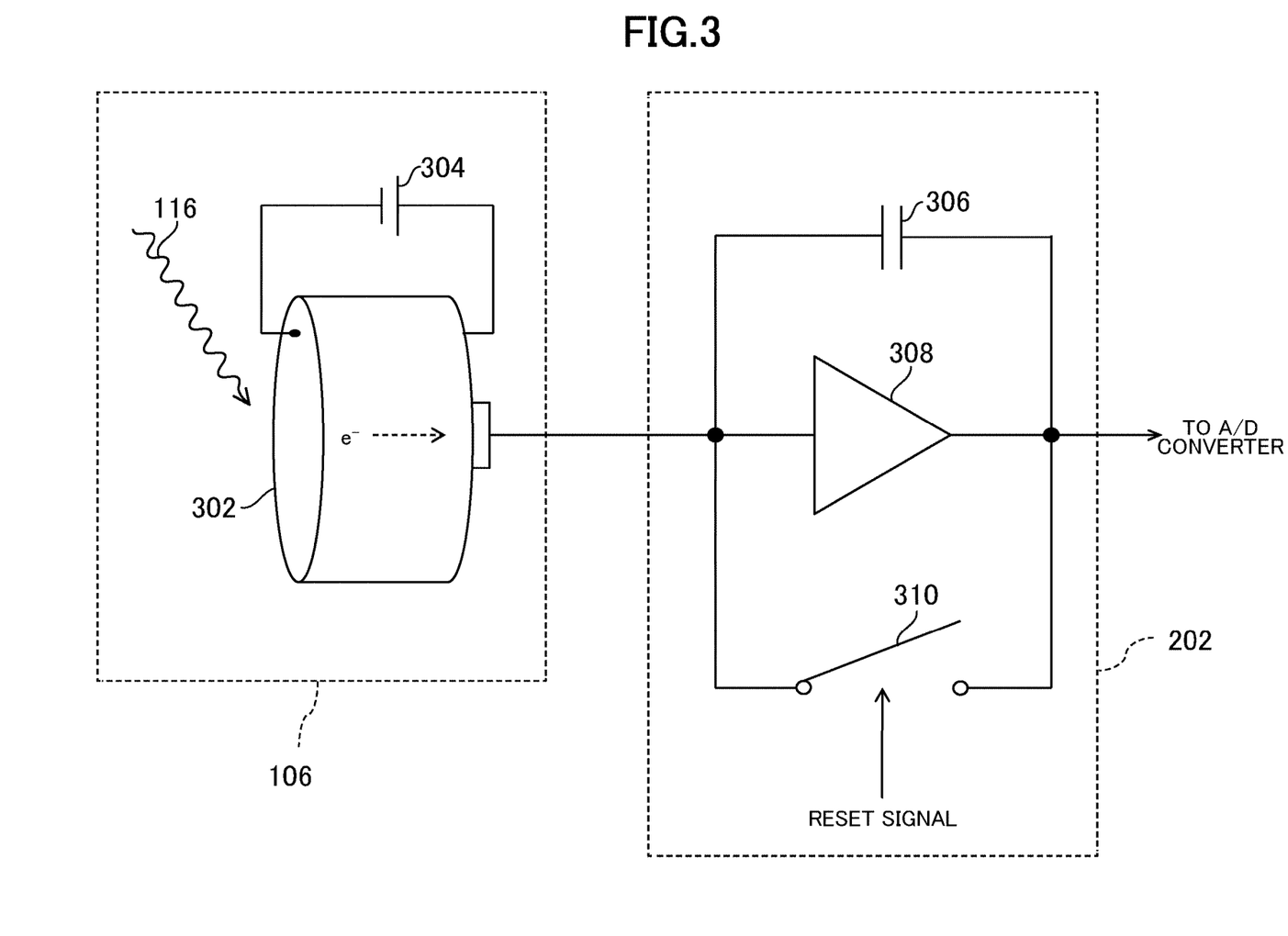
FIG. 3 is a diagram for schematically illustrating a semiconductor detector and a preamplifier.

FIG. 3 is a diagram for illustrating at least one embodiment in which the semiconductor detector 106 is an SDD detector and the preamplifier 202 is an active reset preamplifier. The semiconductor detector 106 includes an SDD device 302 and a voltage source 304. The SDD device 302 includes an anode, a cathode, and a semiconductor layer provided between the anode and the cathode. The voltage source 304 applies a predetermined voltage to the anode and the cathode. When the secondary X-rays 116 enter the SDD device 302, the charge corresponding to the energy of the secondary X-rays 116 is generated in the semiconductor layer due to an ionizing action.

When a predetermined voltage is applied to the anode and the cathode, a leakage current flows between the anode and the cathode. Therefore, the current generated by the semiconductor detector 106 includes a current based on the charge generated by the secondary X-rays 116 and a leakage current generated steadily in the semiconductor detector 106. The magnitude of the leakage current is small when the semiconductor detector 106 is in a normal state. However, the leakage current increases as the semiconductor detector 106 becomes further degraded due to, for example, the entering secondary X-rays 116, excessive electrical noise caused by the discharge of the X-ray tube, or other such factors.

The preamplifier 202 time-integrates the charge output from the semiconductor detector 106, and outputs the charge as a voltage signal. Specifically, for example, the preamplifier 202 is a circuit in which a capacitor 306, an operational amplifier 308, and a switch 310 are connected in parallel with one another. The preamplifier 202 time-integrates the charge input from the semiconductor detector 106 by accumulating the charge input from the semiconductor detector 106 in the capacitor 306, and outputs a stepped voltage signal to the A/D converter 206 in the subsequent stage. The preamplifier 202 also generates a reset signal when the voltage signal reaches an upper limit value set within the allowable (or rated) voltage range of the A/D converter 206. Then, the preamplifier 202 brings the switch 310 into an on state to reduce the voltage signal to a lower limit value. The X-ray signal processor 200 may include a differentiating circuit (not shown) in a stage previous to the A/D converter 206.

Figure 4:
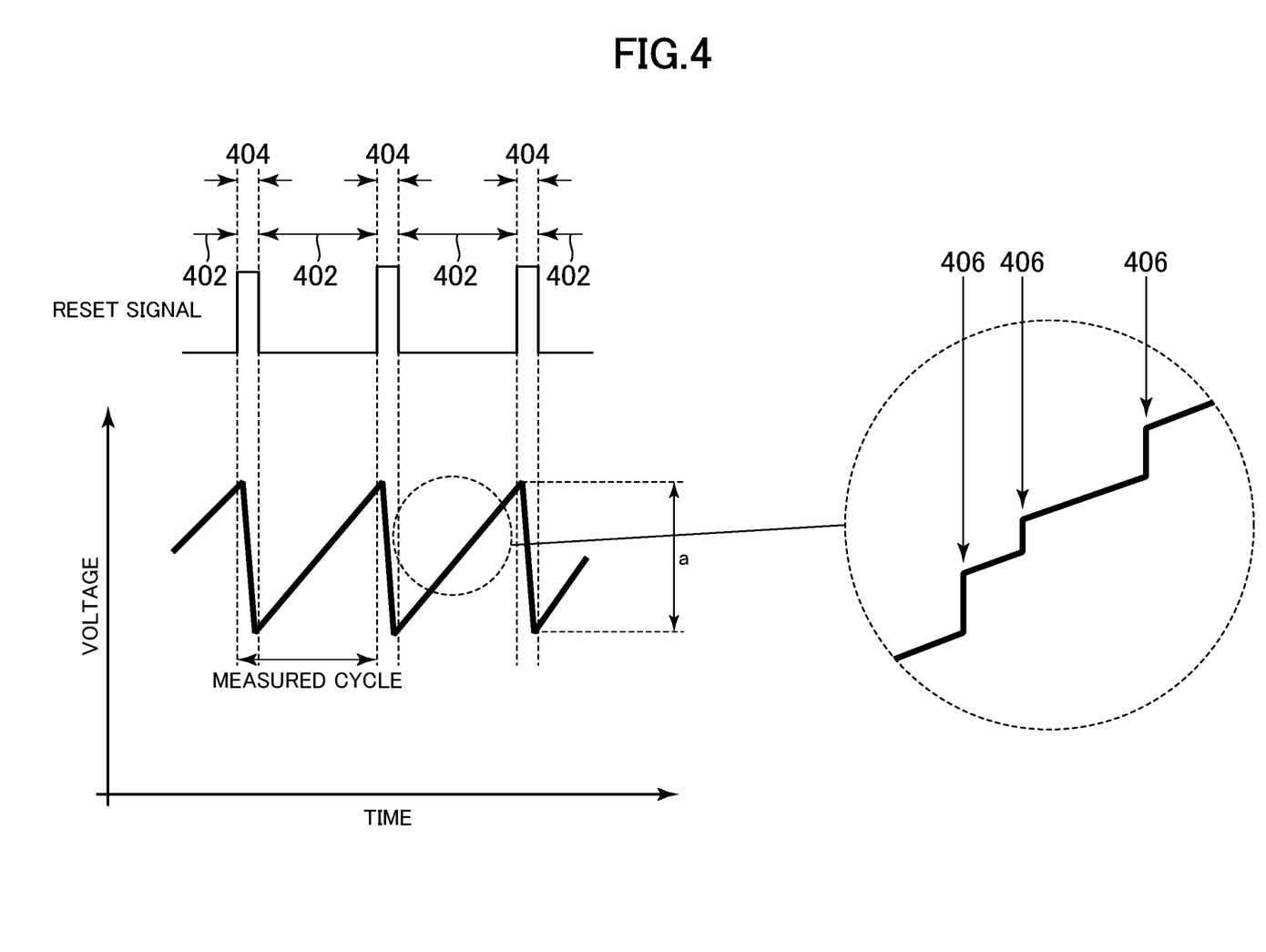
FIG. 4 is a graph for showing an example of a ramp voltage signal.

FIG. 4 is a graph for showing an example of the ramp voltage signal output from the preamplifier 202. Each cycle of the ramp voltage signal includes: a reset period 404 lasting from after the ramp voltage signal reaches the upper limit value until the ramp voltage signal is reduced to the lower limit value; and a detection period 402 other than the reset period 404. Specifically, the detection period 402 is a period during which the voltage of the reset signal input to the switch 310 is an off voltage and the switch 310 is in an off state. Meanwhile, the reset period 404 is a period during which the voltage of the reset signal input to the switch 310 is an on voltage and the switch 310 is in an on state. The reset period 404, which is exaggerated in the graph of FIG. 4, is a fixed time that is much shorter than the detection period 402 in actuality.

In the detection period 402, the ramp voltage signal increases stepwise by being added each time the secondary X-rays 116 are detected by the semiconductor detector 106. As shown in the enlarged graph on the right side of FIG. 4, the detection period 402 includes secondary X-ray detection times 406. The voltage of the ramp voltage signal increases stepwise based on the charge generated by the secondary X-rays 116 at each of the secondary X-ray detection times 406. That is, when the ramp voltage signal is enlarged in the detection period 402, the ramp voltage signal is a stepped wave. Each step of the stepped wave indicates X-rays being detected, and the frequency of the step indicates an X-ray intensity. The height of the step of the stepped wave is proportional to the magnitude of the energy of the detected X-rays.

In each period other than the secondary X-ray detection times 406 within the detection period 402, the voltage of the ramp voltage signal gradually increases based on the leakage current. The magnitude of the slope of the ramp voltage signal is proportional to the magnitude of the leakage current. FIG. 4 is a graph for schematically showing the ramp voltage signal that does not include noise, while an actual ramp voltage signal includes significant noise.

In the reset period 404, the ramp voltage signal drops to a predetermined lower limit value. In the reset period 404, the switch 310 is brought into an on state, and hence both nodes of the capacitor 306 are short-circuited. Therefore, when the charge accumulated in the capacitor 306 is released through the switch 310 that has been brought into an on state, the voltage of the ramp voltage signal is thereby reduced to the lower limit value.

The voltage of the reset signal becomes an on voltage when the voltage of the ramp voltage signal reaches the upper limit value. Meanwhile, the voltage of the reset signal becomes an off voltage when the voltage of the ramp voltage signal reaches the lower limit value. With this setting, the ramp voltage signal has a triangular wave shape as a result of repeatedly increasing and decreasing.

A period of one cycle formed of one reset period 404 and one detection period 402 varies depending on the magnitude of the leakage current in the semiconductor detector 106, and the magnitude and frequency of a stepwise voltage increase due to the charge generated by the entering secondary X-rays 116. That is, the cycle of the ramp voltage signal is not constant. The period of one cycle is measured by the cycle measuring part 216 described later. In the following description, the cycle measured by the cycle measuring part 216 is defined as a measured cycle (T).

Meanwhile, the amplitude of the ramp voltage signal is constant. Specifically, the upper limit value and the lower limit value of the ramp voltage signal are set in advance based on the rated voltages of the capacitor 306 and the operational amplifier 308. Therefore, the amplitude of the ramp voltage signal is a difference between the upper limit value and the lower limit value, and has a constant value. In the following description, the amplitude of the ramp voltage signal is defined as an amplitude (a).

The A/D converter 206 converts the ramp voltage signal that is an analog signal into a ramp voltage signal that is a digital signal. Specifically, the A/D converter 206 converts the ramp voltage signal that is an analog signal output from the preamplifier 202 into a digital signal that can be processed by the waveform shaper 208 and the reset signal detector 214 in the subsequent stage.

The waveform shaper 208 shapes the ramp voltage signal. Specifically, as shown in the enlarged graph of FIG. 4, the ramp voltage signal is a stepped wave when being enlarged in the detection period 402. For example, the waveform shaper 208 shapes each step included in the stepped wave into a trapezoidal wave, a triangular wave, a Gaussian wave, or other such function wave having a pulse height corresponding to the height of the step.

The pulse height analyzer 210 measures the pulse height of the shaped waveform. Specifically, for example, the pulse height analyzer 210 is a multi-channel analyzer, and measures the height of a pulse of the waveform shaped into a trapezoidal wave to acquire the height as a pulse height. For example, the pulse height analyzer 210 converts the pulse height into an energy value for each 10 eV, and discriminates the energy value.

The counter 212 counts the secondary X-rays 116 for each voltage change amount due to the above-mentioned charge based on the ramp voltage signal. Specifically, the counter 212 counts the secondary X-rays 116 for each channel corresponding to the energy of the secondary X-rays 116 based on the pulse height measured by the pulse height analyzer 210. As illustrated in FIG. 2, the counter 212 also generates a histogram 228 representing an acquisition frequency for each kind of energy of the acquired secondary X-rays 116.

The reset signal detector 214 detects a time at which the switch 310 is brought into an on state or an off state. Specifically, for example, the reset signal detector 214 detects the falling edge of the ramp voltage signal. The reset signal detector 214 may also detect the reset signal directly from the preamplifier 202.

The cycle measuring part 216 measures the cycle (measured cycle in FIG. 4) of the ramp voltage signal. Specifically, the cycle measuring part 216 measures a time period between the reset signals detected by the reset signal detector 214. The cycle measuring part 216 may measure the cycle only once when measuring one sample 112, or may acquire the average value of the cycles measured a plurality of times.

Figure 5A:
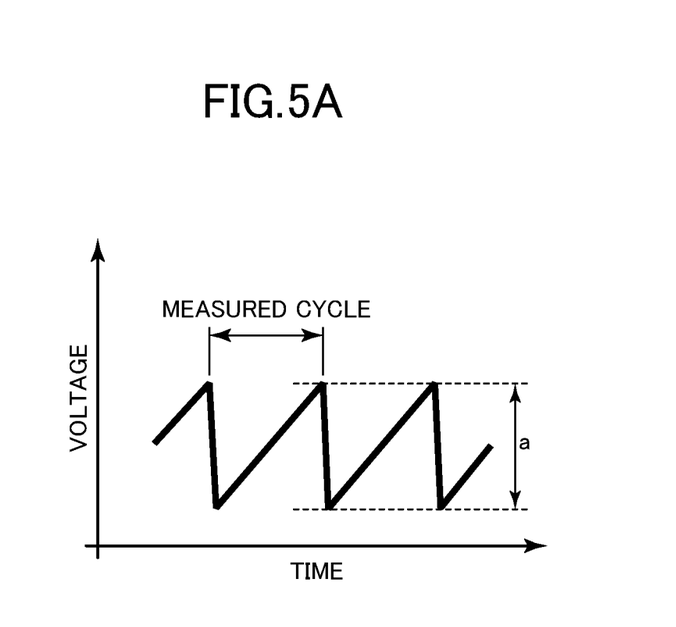
FIG. 5A is an explanatory graph for showing a measured cycle.
Figure 5B:
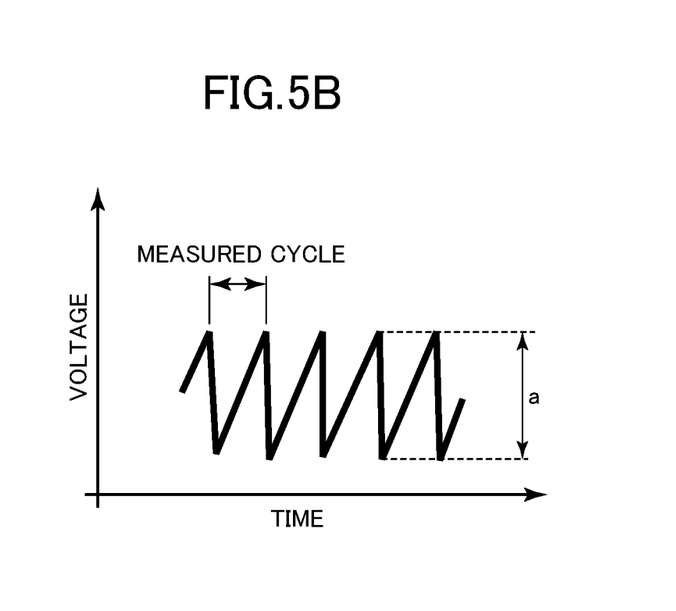
FIG. 5B is an explanatory graph for showing the measured cycle.

The measured cycle varies depending on the magnitude of the leakage current even when the energy and intensity of the X-rays detected by the semiconductor detector 106 are constant, or even when the semiconductor detector 106 has not detected X-rays. Specifically, the measured cycle becomes shorter as the current constantly flowing through the semiconductor detector 106 increases. For example, the measured cycle is long (see FIG. 5A) when the semiconductor detector 106 is in a normal state with a small magnitude of leakage current, and becomes shorter (see FIG. 5B) as the semiconductor detector 106 is further degraded and the leakage current becomes larger in magnitude. The semiconductor detector 106 is damaged by, for example, being irradiated with X-rays for a long period of time, and the leakage current increases. Therefore, the shortness of the measured cycle is a factor indicating the magnitude of damage caused by X-rays.

In addition, the measured cycle is shortened when the semiconductor detector 106 detects the secondary X-rays 116. Specifically, the measured cycle becomes shorter as the frequency (intensity) of the secondary X-rays 116 detected by the semiconductor detector 106 becomes higher or as the energy of the secondary X-rays 116 detected by the semiconductor detector 106 becomes higher. Meanwhile, the measured cycle becomes longer as the frequency (intensity) of the secondary X-rays 116 detected by the semiconductor detector 106 becomes lower or as the energy of the secondary X-rays 116 detected by the semiconductor detector 106 becomes lower.

Figure 6A:
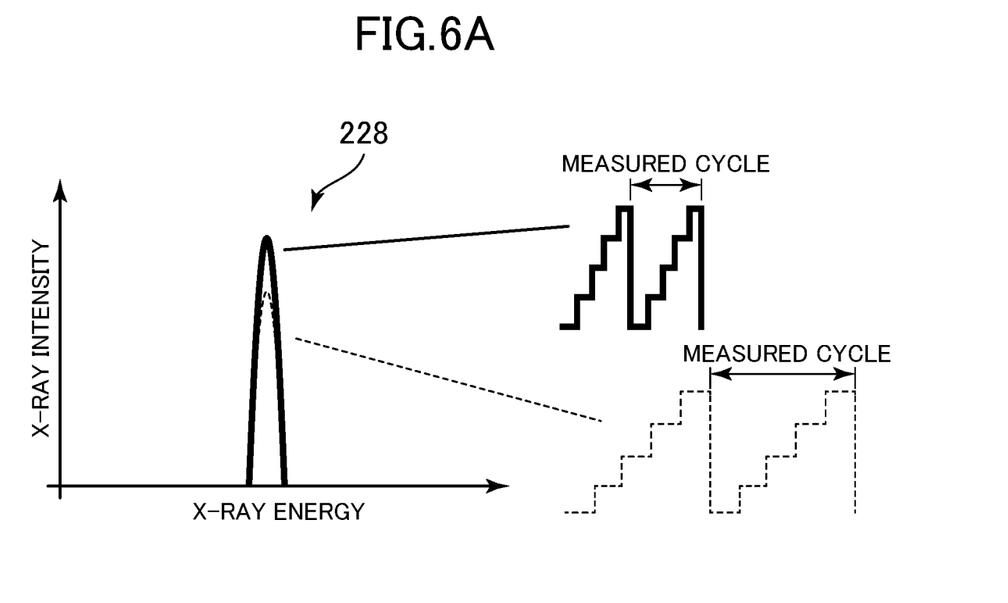
FIG. 6A is an explanatory graph for showing a relationship of the measured cycle with an X-ray intensity and X-ray energy.

FIG. 6A is an explanatory graph for showing a change in measured cycle depending on the frequency of the secondary X-rays 116 when the secondary X-rays 116 having the same energy are measured. The ramp voltage signal obtained when the frequency of the secondary X-rays 116 is high (solid line) has a shorter measured cycle than the ramp voltage signal obtained when the frequency of the secondary X-rays 116 is low (dashed line). The secondary X-rays 116 have the same energy, and hence the counter 212 generates the histograms 228 having different heights depending on the frequency at the same position in the horizontal axis (X-ray energy).

Figure 6B:
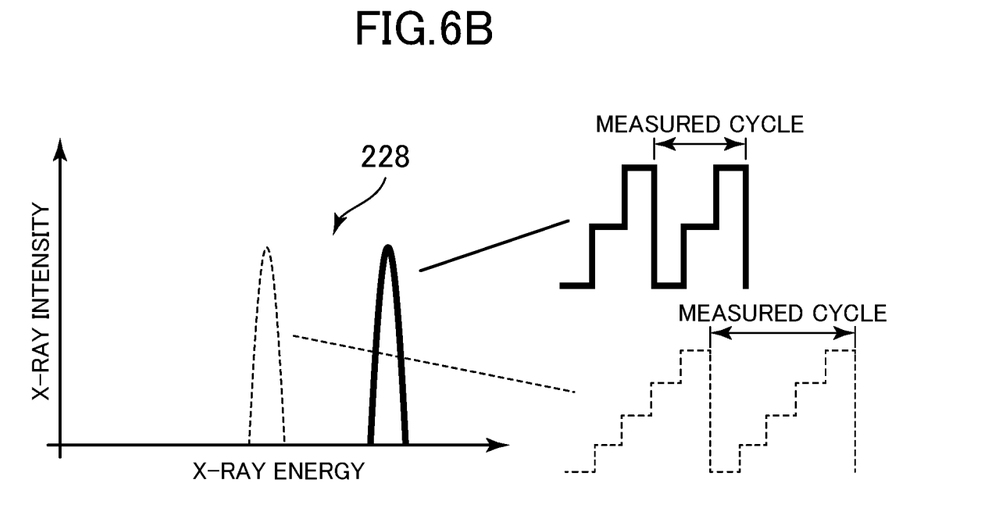
FIG. 6B is an explanatory graph for showing the relationship of the measured cycle with the X-ray intensity and the X-ray energy.

FIG. 6B is an explanatory graph for showing a change in measured cycle depending on the energy of the secondary X-rays 116 when the secondary X-rays 116 having the same frequency are measured. The ramp voltage signal obtained when the energy of the secondary X-rays 116 is high (solid line) has a shorter measured cycle than the ramp voltage signal obtained when the energy of the secondary X-rays 116 is low (dashed line). The secondary X-rays 116 have the same frequency, and hence the counter 212 generates the histograms 228 having the same height at the different positions in the horizontal axis (X-ray energy). For the sake of convenience of description, the height of the step included in the ramp voltage signal is exaggerated in the graphs of FIG. 6A and FIG. 6B.

The arithmetic operation unit 110 includes a calculator 218, a judgment part 220, a storage part 222, a prediction part 224, and an analyzer 226.

The calculator 218 calculates a first voltage change evaluation value and a second voltage change evaluation value. Specifically, for example, the calculator 218 calculates the first voltage change evaluation value corresponding to the total sum of the products of a voltage change amount and its occurrence frequency. When the semiconductor detector 106 is an SDD detector, the amplitude of the ramp voltage signal is represented by a, and the X-ray intensity of each channel of the pulse height analyzer 210 is represented by b. A channel number corresponding to the X-ray energy is represented by k, and the total number of channels is represented by n. An increase amount of the ramp voltage signal ascribable to the leakage current generated in the semiconductor detector 106, which is in a normal state, is represented by $c_0$. In this case, the first voltage change evaluation value is a value obtained by dividing the amplitude of the ramp voltage signal by the sum of the above-mentioned total sum and the value of the leakage current flowing through the semiconductor detector 106 in a normal state. That is, the first voltage change evaluation value is expressed by Expression 1. The first voltage change evaluation value expressed by Expression 1 is a value obtained by dividing the amplitude by the amount of increase in voltage, and therefore represents the cycle of the ramp voltage signal when the semiconductor detector 106 is in a normal state. In this case, $c_0$ is a value calculated in advance as a constant from the constant a and the cycle of the ramp voltage signal when the semiconductor detector 106 does not detect the secondary X-rays 116.

$$\text{First voltage change evaluation value} = \frac{a}{\sum_{k=1}^{n}(k \times b_k) + c_0} \quad \text{(Expression 1)}$$

The second voltage change evaluation value is a value corresponding to the increase amount of the ramp voltage signal. Specifically, the second voltage change evaluation value is a value corresponding to the slope or increase amount of the ramp voltage signal in the detection period 402. The value corresponding to the slope of the ramp voltage signal is, for example, the cycle (measured cycle in FIG. 4) of the ramp voltage signal measured by the cycle measuring part 216. That is, when the cycle of the ramp voltage signal measured by the cycle measuring part 216 is represented by T, the second voltage change evaluation value is expressed by Expression 2.

$$\text{Second voltage change evaluation value} = T \quad \text{(Expression 2)}$$

The judgment part 220 determines whether or not the semiconductor detector 106 has been degraded based on the first voltage change evaluation value and the second voltage change evaluation value. Specifically, the judgment part 220 determines whether or not the semiconductor detector 106 has been degraded based on a first threshold value set in advance and a difference between the first voltage change evaluation value and the second voltage change evaluation value. That is, the judgment part 220 determines that the semiconductor detector 106 has not been degraded when Expression 3 is satisfied, and determines that the semiconductor detector 106 has been degraded when Expression 3 is not satisfied.

$$\frac{a}{\sum_{k=1}^{n}(k \times b_k) + c_0} - T < \text{First threshold value} \quad \text{(Expression 3)}$$

For example, the judgment part 220 determines that the semiconductor detector 106 has not been degraded when the difference between the first voltage change evaluation value and the second voltage change evaluation value is smaller than 1.0, and determines that the semiconductor detector 106 has been degraded when the difference is equal to or larger than 1.0.

The judgment part 220 may also determine whether or not the semiconductor detector 106 has been degraded based on the first threshold value set in advance and a ratio between the first voltage change evaluation value and the second voltage change evaluation value. For example, the judgment part 220 may determine that the semiconductor detector 106 has not been degraded when the ratio between the first voltage change evaluation value and the second voltage change evaluation value is smaller than 10%, and determine that the semiconductor detector 106 has been degraded when the ratio is equal to or larger than 10%.

That is, when the semiconductor detector 106 is in a normal state, the actually measured cycle (second voltage change evaluation value) of the ramp voltage signal should have substantially the same value as the cycle (first voltage change evaluation value) of the ramp voltage signal when the semiconductor detector 106 is in a normal state. However, when the semiconductor detector 106 is degraded and the leakage current flowing through the semiconductor detector 106 increases, the actually measured cycle of the ramp voltage signal is shortened depending on the magnitude of the leakage current. Therefore, the judgment part 220 can determine whether or not the semiconductor detector 106 has been degraded based on the first voltage change evaluation value and the second voltage change evaluation value.

Figure 7:
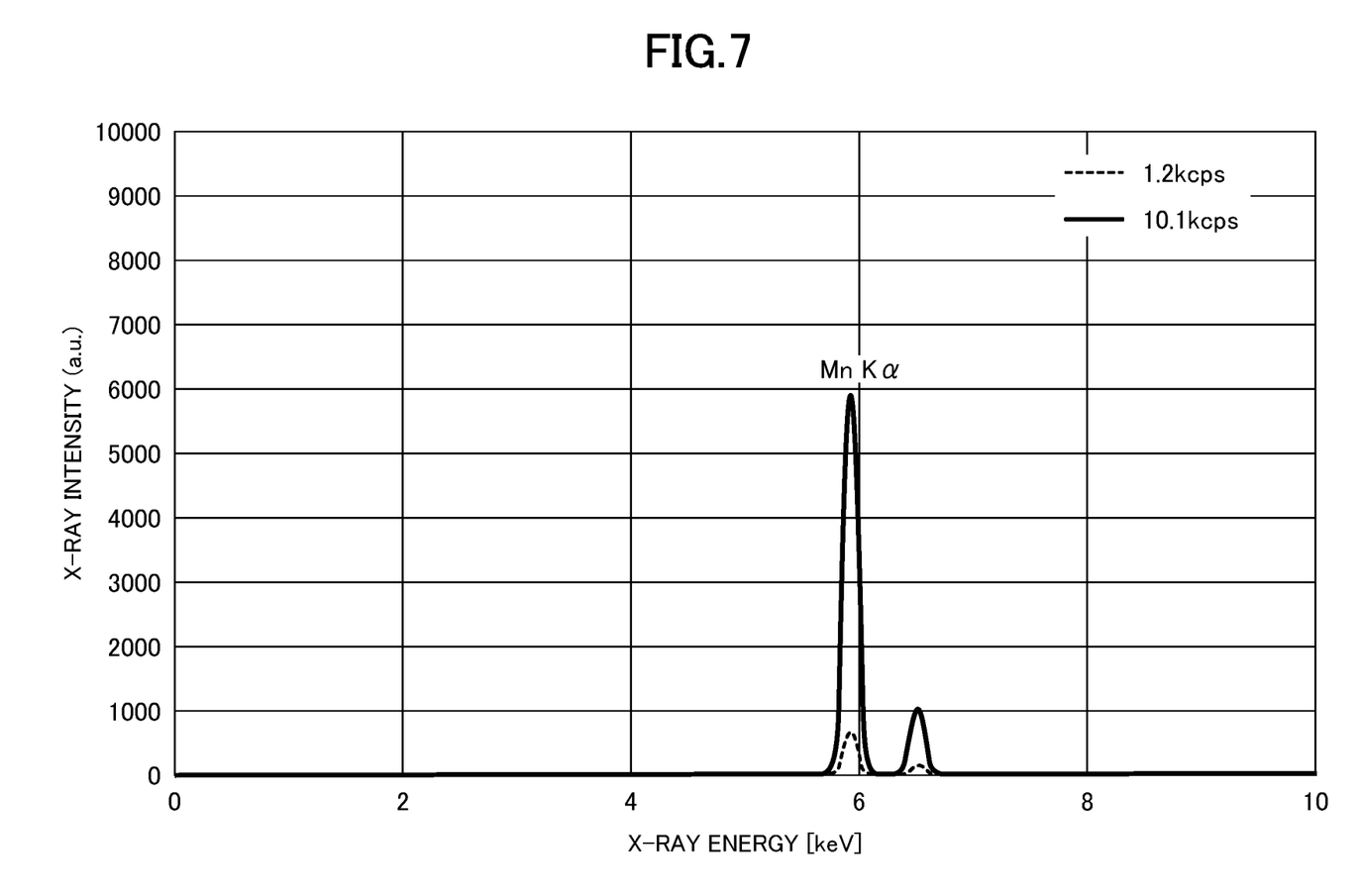
FIG. 7 is a graph for showing an example of a measurement result.

A description will be given of determination to be performed by the judgment part 220 based on an actual measurement result. FIG. 7 is a graph for showing an example of the histogram 228 obtained by the measurement. Measurement conditions under which the measurement result was obtained are as follows. The sample 112 is a Mn sample, and a measuring time period is 10 seconds. Respective X-ray intensities are about 1.2 kcps and about 10.1 kcps. The temperature of the SDD device 302 included in the semiconductor detector 106 is about −30° C. The first voltage change evaluation value and the second voltage change evaluation value calculated from the histogram 228 are shown in Table 1.

TABLE 1

| Mn sample X-ray intensity (kcps) | First voltage change evaluation value (msec) | Second voltage change evaluation value (msec) |
| --- | --- | --- |
| 1.2 | 46.3 | 46.0 |
| 10.1 | 7.7 | 7.6 |

As shown in Table 1, under any one of the experimental conditions, the difference between the first voltage change evaluation value and the second voltage change evaluation value is smaller than 1.0. Therefore, the judgment part 220 determines that the semiconductor detector 106 has not been degraded.

Table 2 is a table for showing the first voltage change evaluation value and the second voltage change evaluation value calculated under the measurement condition that the temperature of the SDD device 302 is about −10° C. As the temperature of the SDD device 302 rises, the leakage current flowing through the semiconductor detector 106 increases. That is, by performing measurement with the temperature of the SDD device 302 being high, it is possible to obtain a measurement result equivalent to that obtained when the semiconductor detector 106 has been degraded. In addition, other measurement conditions are the same as those described above in order to perform a comparison with the above-mentioned measurement result.

TABLE 2

| Mn sample X-ray intensity (kcps) | First voltage change evaluation value (msec) | Second voltage change evaluation value (msec) |
| --- | --- | --- |
| 1.2 | 46.2 | 24.8 |
| 10.1 | 7.6 | 7.5 |

As shown in Table 2, under the experimental condition that the X-ray intensity is 1.2 kcps, the difference between the first voltage change evaluation value and the second voltage change evaluation value is equal to or larger than 1.0. Therefore, the judgment part 220 determines that the semiconductor detector 106 has been degraded.

In the experimental condition that the X-ray intensity is 10.1 kcps, the difference between the first voltage change evaluation value and the second voltage change evaluation value is smaller than 1.0 even if the state under which the temperature of the SDD device 302 is high (that is, state under which the semiconductor detector 106 has been degraded). As the intensity of the secondary X-rays 116 detected by the semiconductor detector 106 increases, the total sum of the products of the voltage change amount and its occurrence frequency increases. As expressed in Expression 1, as the total sum increases, the contribution of the leakage current to the cycle of the ramp voltage signal decreases. There is a possibility that, when the total sum becomes larger, it may be impossible to accurately determine whether or not the semiconductor detector 106 has been degraded.

Accordingly, the judgment part 220 may determine whether or not to perform the determination based on the total sum and a second threshold value set in advance. Specifically, for example, the judgment part 220 performs the determination when Expression 4 is satisfied, and is not required to perform the determination when Expression 4 is not satisfied. Expression 4 indicates that the determination is performed only when the above-mentioned total sum (change amount of the ramp voltage signal ascribable to the secondary X-rays 116) is smaller than a value 10 times (second threshold value) as large as $c_0$ (increase amount of the ramp voltage signal ascribable to the leakage current generated in the semiconductor detector 106 when the semiconductor detector 106 is normal).

$$10c_0 > \Sigma_{k=1}^{n}(k \times b_k) \qquad \text{(Expression 4)}$$

The judgment part 220 may simply perform the determination only when the total sum is smaller than the second threshold value set in advance.

The storage part 222 continuously stores the difference or ratio between the first voltage change evaluation value and the second voltage change evaluation value. Specifically, the storage part 222 stores the difference or ratio for each fixed period. For example, when zero is set at a time when the semiconductor detector 106 is unused, the storage part 222 stores a relationship between a time period during which the semiconductor detector 106 has been used and the difference or ratio obtained when the time period has elapsed.

The prediction part 224 predicts the time at which the semiconductor detector 106 will be degraded from a transition of the stored difference or ratio between the first voltage change evaluation value and the second voltage change evaluation value. Specifically, for example, the prediction part 224 predicts a time at which the above-mentioned difference or ratio becomes larger than the first threshold value based on the relationship between the time and the difference or ratio, which are stored in the storage part 222. In this case, the semiconductor detector 106 is further degraded as the time of irradiation with the secondary X-rays 116 becomes longer, and hence the second voltage change evaluation value becomes smaller as the time for which the semiconductor detector 106 has been used becomes longer. Therefore, by approximating the relationship between the time and the difference or ratio through use of a mathematical function (for example, linear function), the prediction part 224 can predict the above-mentioned time. With this configuration, it is possible to constantly grasp the degree of progress of the performance degradation of the semiconductor detector, and to prevent occurrence of a problem ascribable to the performance degradation.

As described above, as the intensity of the secondary X-rays 116 detected by the semiconductor detector 106 increases, the contribution of the leakage current to the cycle of the ramp voltage signal decreases. In this case, the above-mentioned total sum increases, which leads to a possibility that the prediction part 224 may fail to accurately determine the time at which the semiconductor detector 106 will be degraded. Therefore, the prediction part 224 performs the prediction when Expression 4 is satisfied, and is not required to perform the prediction when Expression 4 is not satisfied.

The analyzer 226 analyzes the elements in the sample 112 based on the counted secondary X-rays 116. Specifically, for example, the analyzer 226 uses the related art to perform qualitative analysis or quantitative analysis on the elements in the sample 112.

As described above, by evaluating the first voltage change evaluation value and the second voltage change evaluation value, it is possible to accurately determine whether or not the semiconductor detector 106 has been degraded, even during measurement. In addition, according to at least one embodiment described above, even when a noise signal is mixed into the output of semiconductor detector 106 and the preamplifier 202, or when the cooling of the semiconductor detector 106 is insufficient, a sudden change occurs in the difference or ratio between the first voltage change evaluation value and the second voltage change evaluation value. By detecting this change, it is possible to determine that a sudden failure has occurred in the semiconductor detector 106.

The present invention can be variously modified without being limited to the above-mentioned embodiment. The configuration is described as one example, and the present invention is not limited thereto. The configuration described in the above-mentioned embodiment may be replaced by configuration that is substantially the same as the configuration described in the above-mentioned embodiment, configuration that exhibits the same action and effect as those of the configuration described in the above-mentioned embodiment, or configuration that achieves the same object as that of the configuration described in the above-mentioned embodiment.

For example, the X-ray spectrometer 100 according to at least one embodiment is an apparatus configured to irradiate the sample 112 with the primary X-rays 114 to detect the secondary X-rays 116 emitted from the sample 112, but may be an apparatus configured to detect X-rays diffracted or scattered by the sample 112.

The exciting lines for exciting the sample are not limited to the primary X-rays 114, and electron beams, proton beams, or other such charged particle beams may be used as the exciting lines. Specifically, in place of the X-ray source 104 configured to generate the primary X-rays 114 as the exciting lines, the X-ray spectrometer 100 may include a charged particle beam source (for example, electron gun, particle accelerator, or radiation source) configured to generate charged particle beams as the exciting lines. The semiconductor detector 106 to be used is, for example, an SDD detector, a Si (Li) detector, a Si-PIN detector, or a CdTe detector, and its type is not particularly limited.

The first voltage change evaluation value and the second voltage change evaluation value are not limited to those described above. For example, while the first voltage change evaluation value is the total sum of the products of the voltage change amount and its frequency of occurrence (Expression 5), the second voltage change evaluation value may be the cycle of the ramp voltage signal measured by the cycle measuring part 216 (Expression 2).

First voltage change evaluation value=$\sum_{k=1}^{n}(k \times b_k)$ (Expression 5)

Then, the judgment part 220 may determine whether or not the semiconductor detector 106 has been degraded based on a value obtained by subtracting the first voltage change evaluation value from the value obtained by dividing the amplitude of the ramp voltage signal by the second voltage change evaluation value. Specifically, when the cycle of the ramp voltage signal measured by the cycle measuring part 216 is represented by T, an increase amount c of the ramp voltage signal ascribable to the leakage current generated in the semiconductor detector 106 is expressed by Expression 6. The right-hand side of Expression 6 is the value obtained by subtracting the first voltage change evaluation value from the value obtained by dividing the amplitude a of the ramp voltage signal by the second voltage change evaluation value.

$$c = \frac{a}{T} - \sum_{k=1}^{n}(k \times b_k)$$ (Expression 6)

When the increase amount of the ramp voltage signal ascribable to the leakage current generated in the semiconductor detector 106, which is in a normal state, is represented by $c_0$, the degree of degradation of the semiconductor detector 106, that is, a change in leakage current ascribable to the degradation, corresponds to a difference between c and $c_0$. Therefore, the judgment part 220 may determine that the semiconductor detector 106 has not been degraded when the difference is smaller than the first threshold value set in advance (when Expression 7 is satisfied).

$c-c_0$<First threshold value (Expression 7)

When the semiconductor detector 106 has been degraded, the leakage current flowing through the semiconductor detector 106 increases. As described above, the judgment part 220 may calculate the magnitude of the leakage current through use of the first voltage change evaluation value and the second voltage change evaluation value, to thereby determine whether or not the semiconductor detector 106 has been degraded.

In this case as well, the judgment part 220 may determine whether or not to perform the determination based on the total sum and the second threshold value set in advance. The storage part 222 may also continuously store the difference or ratio between c and $c_0$. Then, the prediction part 224 may predict the time at which the semiconductor detector 106 will be degraded from the transition of the stored difference or ratio. In addition, the prediction part 224 performs the prediction when Expression 4 is satisfied, and is not required to perform the prediction when Expression 4 is not satisfied.

The X-ray signal processor 200 may also include a notifier configured to notify a user that the semiconductor detector 106 has been degraded. Specifically, for example, the notifier is a display apparatus configured to display a result determined by the judgment part 220. The notifier may be a speaker configured to issue an alarm to the user when the judgment part 220 determines that the semiconductor detector 106 has been degraded. The notifier may also notify the user of the time at which the semiconductor detector 106 will be degraded, which has been predicted by the prediction part 224.

While there have been described what are at present considered to be certain embodiments of the invention, it will be understood that various modifications may be made thereto, and it is intended that the appended claims cover all such modifications as fall within the true spirit and scope of the invention.

EXPLANATION OF REFERENCES

100 X-ray spectrometer, 102 sample stage, 104 X-ray source, 106 semiconductor detector, 108 processing unit, 110 arithmetic operation unit, 112 sample, 114 primary X-rays, 116 secondary X-rays, 200 X-ray signal processor, 202 preamplifier, 206 A/D converter, 208 waveform shaper, 210 pulse height analyzer, 212 counter, 214 reset signal detector, 216 cycle measuring part, 218 calculator, 220 judgment part, 222 storage part, 224 prediction part, 226 analyzer, 228 histogram, 302 SDD device, 304 voltage source, 306 capacitor, 308 operational amplifier, 310 switch, 402 detection period, 404 reset period, 406 secondary X-ray detection times.

What is claimed is:

1. An X-ray signal processor, comprising:
a semiconductor detector configured to generate a charge corresponding to energy of detected X-rays;
a preamplifier configured to output a ramp voltage signal corresponding to the generated charge;
a counter configured to count the X-rays for each voltage change amount due to the charge based on the ramp voltage signal; and
a judgment part configured to determine whether the semiconductor detector has been degraded based on a first voltage change evaluation value corresponding to a total sum of products of the voltage change amount and an occurrence frequency thereof, and a second voltage change evaluation value corresponding to an increase amount of the ramp voltage signal.

2. The X-ray signal processor according to claim 1, wherein the first voltage change evaluation value includes a value obtained by dividing an amplitude of the ramp voltage signal by a sum of the total sum and a value of a leakage current flowing through the semiconductor detector in a normal state.

3. The X-ray signal processor according to claim 1, wherein each cycle of the ramp voltage signal includes:
a reset period lasting from after the ramp voltage signal reaches an upper limit value until the ramp voltage signal is reduced to a lower limit value; and
a detection period other than the reset period, and
wherein the second voltage change evaluation value includes a value corresponding to one of a slope and the increase amount of the ramp voltage signal in the detection period.

4. The X-ray signal processor according to claim 3, further comprising a cycle measuring part configured to measure a cycle of the ramp voltage signal,
wherein the second voltage change evaluation value includes the cycle of the ramp voltage signal measured by the cycle measuring part, and
wherein the judgment part is configured to determine whether the semiconductor detector has been degraded based on a first threshold value set in advance and one of a difference or a ratio between the first voltage change evaluation value and the second voltage change evaluation value.

5. The X-ray signal processor according to claim 4, wherein the judgment part is configured to determine whether to perform the determination based on the total sum and a second threshold value set in advance.

6. The X-ray signal processor according to claim 4, further comprising:
a storage part configured to continuously store one of the difference or the ratio between the first voltage change evaluation value and the second voltage change evaluation value; and
a prediction part configured to predict a time at which the semiconductor detector will be degraded from a transition of the stored one of the difference or the ratio.

7. The X-ray signal processor according to claim 1, further comprising a cycle measuring part configured to measure a cycle of the ramp voltage signal,
wherein the first voltage change evaluation value includes the total sum,
wherein the second voltage change evaluation value includes the cycle of the ramp voltage signal measured by the cycle measuring part, and
wherein the judgment part is configured to determine whether the semiconductor detector has been degraded based on a value obtained by subtracting the first voltage change evaluation value from a value obtained by dividing an amplitude of the ramp voltage signal by the second voltage change evaluation value.

8. An X-ray spectrometer, comprising:
a semiconductor detector configured to detect X-rays emitted by irradiating a sample with exciting lines, to thereby generate a charge corresponding to energy of the X-rays;
a preamplifier configured to output a ramp voltage signal corresponding to the generated charge;
a counter configured to count the X-rays for each voltage change amount due to the charge based on the ramp voltage signal;
a judgment part configured to determine whether the semiconductor detector has been degraded based on a first voltage change evaluation value corresponding to a total sum of products of the voltage change amount and an occurrence frequency thereof, and a second voltage change evaluation value corresponding to an increase amount of the ramp voltage signal; and
an analyzer configured to analyze elements in the sample based on the counted X-rays.

* * * * *